United States Patent [19]

Wootten et al.

[11] 4,282,758
[45] Aug. 11, 1981

[54] INDIVIDUAL LEAD PULL TEST FOR BEAM LEADED DEVICES

[75] Inventors: Richard M. Wootten, Huntsville, Ala.; Jake Herron, Jr., Niceville, Fla.

[73] Assignee: The United States of America as represented by the Secretary of the Army, Washington, D.C.

[21] Appl. No.: 105,839

[22] Filed: Dec. 20, 1979

[51] Int. Cl.³ ............................................. G01N 3/08
[52] U.S. Cl. ................................................... 73/827
[58] Field of Search ................ 73/827, 834, 826, 828, 73/830; 228/103, 104, 56.5

[56] References Cited

U.S. PATENT DOCUMENTS

| | | | |
|---|---|---|---|
| 3,564,911 | 2/1971 | Slemmons et al. | 73/827 X |
| 3,572,108 | 3/1971 | McShane et al. | 73/827 X |
| 3,945,248 | 3/1976 | West | 73/827 |

Primary Examiner—Jerry W. Myracle
Attorney, Agent, or Firm—Nathan Edelberg; Robert P. Gibson; James T. Deaton

[57] ABSTRACT

A method for destructive testing of the bond strength of each individual lead of a chip beam-lead device which includes cutting the chip using a laser, laser cutting a hole through each individual piece of the chip with the lead attached to the chip and inserting a hook of a pull tester into the hole made in each chip section and pulling the chip section and the lead attached thereto to determine the bond strength between the lead of the chip and the conductor to which the lead is attached.

3 Claims, 4 Drawing Figures

INDIVIDUAL LEAD PULL TEST FOR BEAM LEADED DEVICES

DEDICATORY CLAUSE

The invention described herein may be manufactured, used, and licensed by or for the Government for governmental purposes without the payment to us of any royalties thereon.

BACKGROUND OF THE INVENTION

The present technology involving the testing of beam-lead devices deals with the "push-off" testing of the entire bonding of the multiplicity of leads at one time. This technology involves the use of a special substrate arranged such that a hole is directly under the bonded beam-lead device in order to allow the "push-off" test to be accomplished. When the bonded beam lead device is desired to be tested with the prior art method, the force required to separate the bonded beam leads of the device from the conductor pattern is recorded and the recorded force is then divided by the number of beam-leads of the bonded beam leaded device to determine the calculated bond strength of each beam-lead. As can be seen, this method is not very accurate since it is no more accurate than the average force required to separate each individual lead. Since all the beam-leads are separated by a single force, there is no way to accurately determine the actual bond strength of each beam lead to its respective conductor.

Therefore, it is an object of this invention to provide a method for testing the bond strength of each individual beam lead to its respective conductor.

Another object of this invention is to test the tensile strength of each individual lead.

Still another object of this invention is to determine if sufficient bond strength of an individual lead to its conductor has been attained.

Yet another object of this invention is to provide a method of testing an individual lead in a more accurate manner than previously done and thereby result in a method that leaves no errors in assumptions.

Other objects of this invention will be obvious to those skilled in this art.

SUMMARY OF THE INVENTION

In accordance with this invention, a method for destructive testing of beam-leaded devices is provided in which a ceramic chip of a beam-leaded integrated circuit is cut with a laser to segment a portion of the ceramic chip with each individual beam-lead, then cutting a hole with the laser through each individually cut chip section and then attaching a hook of a gram pull tester in the hole of each individual chip section and pulling on the tester until the bond between the individual beam lead and the conductor to which each individual beam lead is connected is broken or the beam lead itself is broken to test the bond strength of each individual beam-lead to its respective conductor. In this manner, the bond strength of each individual beam-lead to its respective conductor is accurately tested to determine the sufficiency of the bond strength of each individual lead.

DESCRIPTION OF THE EMBODIMENT

Figure 1:
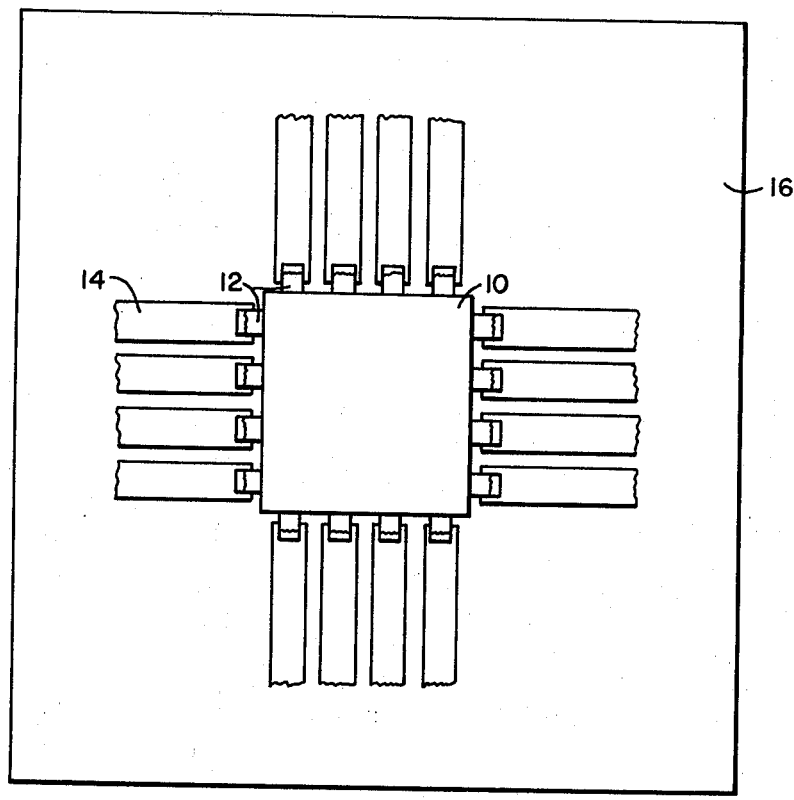
FIG. 1 is a top plan view of a typical beam-lead device on circuit with portions cut away.

Referring now to the drawing, in FIG. 1 a chip beam-lead device 10 is made of a ceramic material and has a multiplicity of circuits mounted therein and relative thereto. Chip beam-lead device 10 also has a plurality of gold beam-leads 12 leading therefrom with each beam lead 12 being connected by diffusion bonding to a gold lead 14 mounted on substrate material 16. To illustrate the smallness of these devices, ten of the chip beam-lead devices 10 are connected to conductors on a one-inch square. That is, this invention is related to integrated circuit devices of very small dimension.

Figure 2:
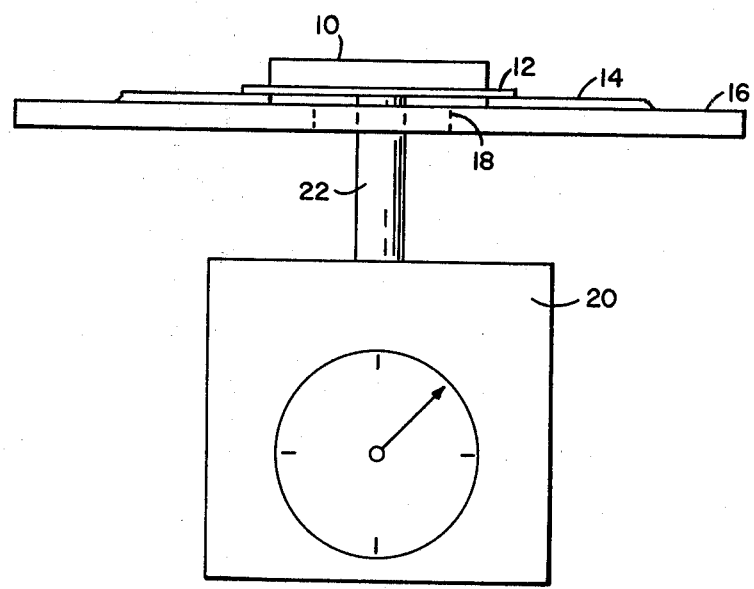
FIG. 2 is a schematic view of a test arrangement of the prior known testing method.

Referring now to FIG. 2, a prior art test arrangement is illustrated in which substrate 16 has an opening 18 therethrough and a gram push tester 20 has a shaft 22 positioned through opening 18 and onto a bottom surface of chip beam-lead device 10 to exert force thereon and test the bond strength of beam-leads 12 collectively. That is, gram push tester 20 has force applied through shaft 22 to chip beam-lead device 10 with all of beam-leads 12 connected to their respective conductors 14 to give an overall reading on gram push tester 12 of the force required to either break chip beam-lead device 10, or break beam-leads 12 or separate beam-leads 12 where they are bonded to conductors 14. As can be seen in this prior art arrangement, the actual bond strength of each beam-lead 12 to its respective conductor 14 can only be approximated since an average of the force required to perform the test can be asserted for each individual beam-lead.

Figure 3:
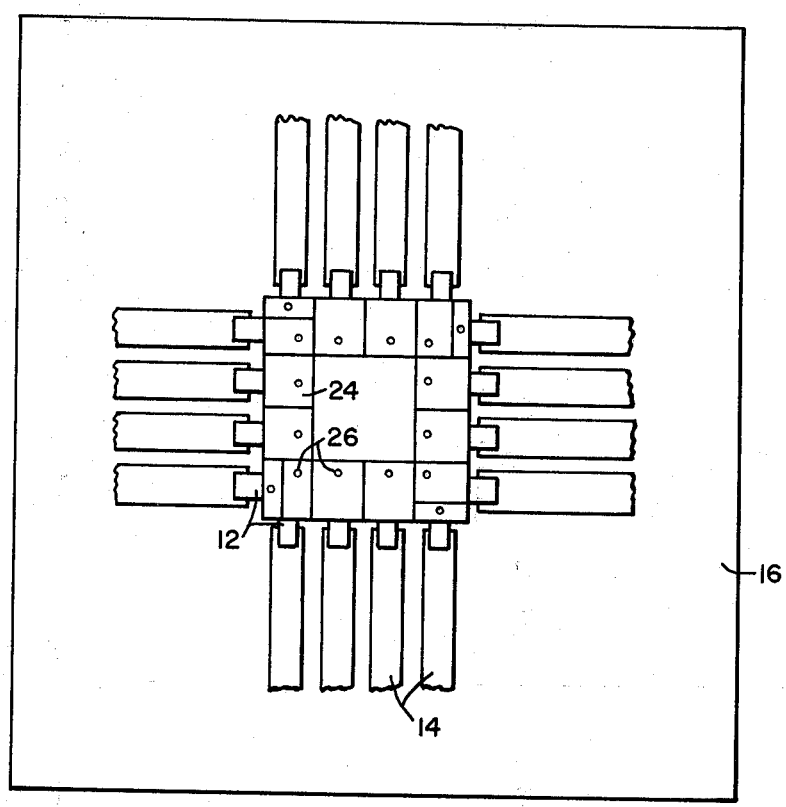
FIG. 3 is a top plan view illustrating a ceramic chip that has been cut into individual pieces and provided with holes cut therein to enable the leads to be pulled.
Figure 4:
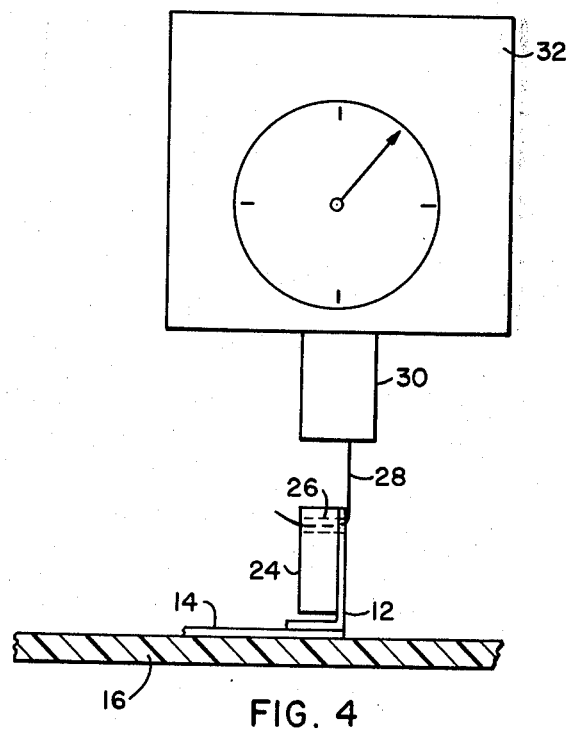
FIG. 4 is a side view illustrating a gram pull tester connected to the individual section of the ceramic chip to perform the gram pull test.

Referring now to FIG. 3, chip beam-lead device 10 is illustrated as being laser cut into sections 24 with a laser section 24 remaining on each lead 12. A hole 26 is then cut with a laser through each section 24 adjacent to its respective beam-lead. Each beam-lead is then bent upward to facilitate placing test hook 28 (See FIG. 4) through hole 26 of the desired beam-lead to be tested. Hook 28 is connected to shaft 30 of pull tester 32 to indicate the force exerted on the respective beam-lead 12 that is required to either break beam-lead 12 or separate the beam-lead from its respective conductor 14. The force required to break or detach the respective beam-lead from its conductor is recorded to give an accurate indication of the bond strength of the respective beam-lead to its conductor. As can be seen, this method of testing even though a destructive type method gives a complete and accurate test for the bond strength of each beam-lead 12 relative to its respective conductor 14. This is what is desired and has been needed in this art for some time.

We claim:

1. A method for testing individual beam-leads of a chip-beam leaded device that has a multiplicity of beam-leads bonded to respective conductors that are mounted on a substrate, said method comprising cutting said chip beam-leaded device into sections so that a beam-lead remains on each section, then cutting a hole through each cut section at a position adjacent to said beam-lead, placing a hook of a gram pull tester through said hole in said cut section and pulling said gram pull tester until said beam-lead breaks or is separated from said conductor to determine the bond strength of said beam-lead relative to said conductor.

2. A method as set forth in claim 1, wherein said chip beam-leaded device is cut using a laser cutting device, and said hole is placed each section using said laser cutting device.

3. A method as set forth in claim 1, wherein said section having the beam-lead connected thereto is turned upward prior to said test hook being inserted through said hole.

* * * * *